(12) United States Patent
Wallenstein et al.

(10) Patent No.: US 10,426,630 B2
(45) Date of Patent: Oct. 1, 2019

(54) SPINAL IMPLANT

(71) Applicant: K2M, Inc., Leesburg, VA (US)

(72) Inventors: Todd Wallenstein, Ashburn, VA (US); Jennifer Moore, Summit Point, WV (US)

(73) Assignee: K2M, Inc., Leesburg, VA (US)

( * ) Notice: Subject to any disclaimer, the term of this patent is extended or adjusted under 35 U.S.C. 154(b) by 923 days.

(21) Appl. No.: 14/620,788

(22) Filed: Feb. 12, 2015

(65) Prior Publication Data

US 2015/0223950 A1 Aug. 13, 2015

Related U.S. Application Data

(60) Provisional application No. 61/938,725, filed on Feb. 12, 2014.

(51) Int. Cl.
*A61F 2/44* (2006.01)
*A61F 2/30* (2006.01)
*A61B 17/80* (2006.01)
*A61B 17/86* (2006.01)

(52) U.S. Cl.
CPC ........ *A61F 2/4455* (2013.01); *A61B 17/8047* (2013.01); *A61B 17/86* (2013.01); *A61F 2002/3008* (2013.01); *A61F 2002/30149* (2013.01); *A61F 2002/30787* (2013.01); *A61F 2002/30827* (2013.01); *A61F 2002/30904* (2013.01); *A61F 2002/4475* (2013.01)

(58) Field of Classification Search
CPC .......... A61F 2/4455; A61F 2002/30787; A61F 2002/30149; A61F 2230/0017; A61F 2220/0008; A61F 2220/0016; A61F 2230/0063; A61B 17/8047; A61B 17/7067
See application file for complete search history.

(56) References Cited

U.S. PATENT DOCUMENTS

| 5,397,364 | A |  | 3/1995 | Kozak et al. |
| 6,039,761 | A | * | 3/2000 | Li .......................... A61F 2/4455 623/17.16 |
| 6,235,059 | B1 |  | 5/2001 | Benezech et al. |
| 6,342,074 | B1 |  | 1/2002 | Simpson |
| 6,432,106 | B1 |  | 8/2002 | Fraser |
| 6,471,724 | B2 |  | 10/2002 | Zdeblick et al. |
| 6,629,998 | B1 |  | 10/2003 | Lin |
| 6,972,019 | B2 |  | 12/2005 | Michelson |

(Continued)

*Primary Examiner* — Brian E Pellegrino
(74) *Attorney, Agent, or Firm* — Lerner, David, Littenberg, Krumholz & Mentlik, LLP

(57) ABSTRACT

A spinal implant configured for positioning within a space between adjacent vertebral bodies includes first and second bone screws and a body. The body includes a back surface having first and second openings for receiving the first and second screws. The first and second openings are configured for orientation towards opposing vertebral bodies. The body further includes first and second side surfaces extending from opposing ends of the back surface and first and second end surfaces extending from respective first and second side surfaces, wherein the ends of the first and second end surfaces meet and define an atraumatic nose. A first angle is formed between the first side surface and the first end surface that is different than a second angle that is formed between the second side surface and the first end surface. A method using same is also disclosed.

5 Claims, 9 Drawing Sheets

(56) References Cited

U.S. PATENT DOCUMENTS

| | | | |
|---|---|---|---|
| 6,984,234 | B2 | 1/2006 | Bray |
| 7,033,394 | B2 | 4/2006 | Michelson |
| 7,041,135 | B2 | 5/2006 | Michelson |
| 7,077,864 | B2 | 7/2006 | Byrd, III et al. |
| 7,112,222 | B2 | 9/2006 | Fraser et al. |
| 7,163,561 | B2 | 1/2007 | Michelson |
| 7,172,627 | B2 | 2/2007 | Fiere et al. |
| 7,226,482 | B2 | 6/2007 | Messerli et al. |
| 7,232,463 | B2 | 6/2007 | Falahee |
| 7,232,464 | B2 | 6/2007 | Mathieu et al. |
| 7,435,262 | B2 | 10/2008 | Michelson |
| 7,815,681 | B2 | 10/2010 | Ferguson |
| 7,846,207 | B2 | 12/2010 | Lechmann et al. |
| 7,850,731 | B2 | 12/2010 | Brittan et al. |
| 7,972,363 | B2 | 7/2011 | Moskowitz et al. |
| 8,137,405 | B2 | 3/2012 | Kostuik et al. |
| 8,187,329 | B2 | 5/2012 | Theofilos |
| 2003/0130737 | A1 | 7/2003 | McGahan et al. |
| 2005/0177245 | A1 | 8/2005 | Leatherbury et al. |
| 2008/0183293 | A1 | 7/2008 | Parry et al. |
| 2008/0249569 | A1 | 10/2008 | Waugh et al. |
| 2008/0249575 | A1 | 10/2008 | Waugh et al. |
| 2008/0249625 | A1 | 10/2008 | Waugh et al. |
| 2008/0294262 | A1 | 11/2008 | Levieux |
| 2008/0306596 | A1 | 12/2008 | Jones et al. |
| 2009/0105831 | A1 | 4/2009 | Jones et al. |
| 2009/0210062 | A1 | 8/2009 | Thalgott et al. |
| 2012/0277873 | A1 | 11/2012 | Kana et al. |
| 2014/0148905 | A1 | 5/2014 | Messerli et al. |
| 2014/0214166 | A1 | 7/2014 | Theofilos |
| 2015/0164653 | A1 | 6/2015 | Kueenzi et al. |

\* cited by examiner

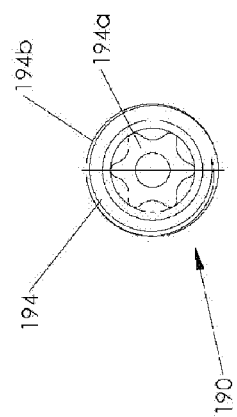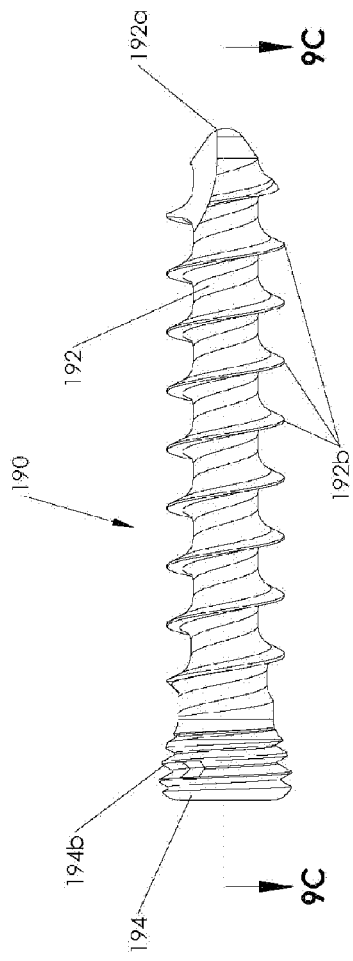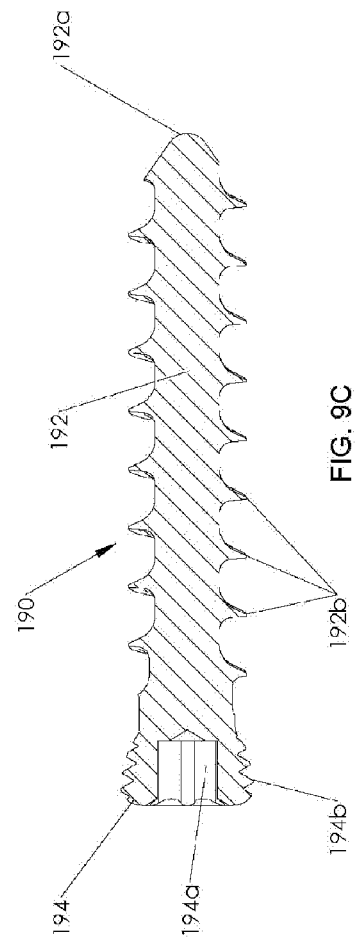
FIG. 9A
FIG. 9B
FIG. 9C

SPINAL IMPLANT

CROSS-REFERENCE TO RELATED APPLICATION

This application claims priority to, and the benefit of, U.S. Provisional Patent Application Ser. No. 61/938,725, filed on Feb. 12, 2014, the entire contents of which are incorporated by reference herein.

TECHNICAL FIELD

The present disclosure relates generally to devices and methods for treating spinal conditions, and in particular, to spinal implants configured for positioning within an intervertebral space.

BACKGROUND

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as intervertebral discs. Intervertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

Disorders of the spine that may cause misalignment of the vertebrae or constriction of the spinal canal include spinal injuries, infections, tumor formation, herniation of the intervertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina, i.e., the bony roof of the spinal canal. Discectomy involves partial or complete removal of the intervertebral discs. Corpectomy involves removal of the vertebral body as well as the adjacent intervertebral discs.

The time-honored method of addressing the issues of neural irritation and instability resulting from severe disc damage have largely focused on removal of the damaged disc and fusing the adjacent vertebral elements together. Removal of the disc relieves the mechanical and chemical irritation of neural elements, while osseous union (bone knitting) solves the problem of instability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration, expulsion, or nonunion due to structural failures of the bone or residual degrees of motion that retard or prohibit bony union. Therefore, intervertebral prostheses in various forms have been used to provide immediate stability and to protect and preserve an environment that fosters growth of grafted bone such that a structurally significant bony fusion can occur.

Many intervertebral implants are formed from biocompatible materials, such as titanium. However, such materials are rigid and provide minimal cushioning. Such rigidity, in extreme situations, may be a cause of subsidence, which can generate additional pain and trauma to a spinal column.

Therefore, a need exists for an intervertebral implant that provides cushioned support and remains in place during use.

SUMMARY

The present disclosure relates to spinal implants configured for positioning within an intervertebral space. The spinal implant includes first and second bone screws and a body. The body includes a back surface having first and second openings for receiving the first and second screws. The first opening is configured for orientation towards a first vertebral body and the second opening is configured for orientation towards a second vertebral body. The body also includes first and second side surfaces extending from opposing ends of the back surface and first and second end surfaces extending from the respective first and second side surfaces. The ends of the first and second end surfaces meet and define an atraumatic nose. A first angle is formed between the first side surface and the first end surface and a second angle is formed between the second side surface and the first end surface. The first angle is different than the second angle.

In aspects, the first end surface defines a first longitudinal axis. The first longitudinal axis bisects the first end surface and extends perpendicular therefrom. The body is asymmetrical about the first longitudinal axis.

In aspects, the back surface defines a second longitudinal axis extending perpendicular therefrom. The back surface is oriented relative to the first end surface such that the second longitudinal axis defines an oblique angle with respect to the first longitudinal axis.

In aspects, the second angle is greater than the first angle.

In aspects, the back surface, the first and second end surfaces, and the first and second side surfaces define top and bottom surfaces. The top and bottom surfaces include ridges adapted to engage the first and second vertebral bodies.

In aspects, at least one insert slot is defined in one of the top and bottom surfaces. The at least one insert slot is in communication with a corresponding opening of the first and second openings and is configured to receive a plate insert.

In aspects, the plate insert includes a screw opening defined therethrough. The plate insert is configured to be received within the at least one insert slot with the screw opening substantially aligned with a corresponding opening of the first and second openings of the body.

In aspects, a through-bore is defined through the top and bottom surfaces of the body.

In aspects, the body includes a body portion and a plate.

In aspects, the plate includes a leading surface defined opposite the back surface that includes a T-shaped projection.

In aspects, the body portion includes a trailing surface defined opposite the first end surface. The trailing surface is configured to mate with the leading surface of the plate and includes a T-shaped slot defined therein. The T-shaped slot is configured to slidably engage the T-shaped projection of the plate, thereby permitting the plate and the body portion to be selectively engaged.

In aspects, the T-shaped projection and the T-shaped slot are oriented such that when the body portion and plate are slidably engaged, the body portion and the plate are prevented from moving relative to each other in a caudal or cephalad direction.

In aspects, the body portion is formed of a material that is softer than that of the plate material.

A method of performing surgery is also disclosed. The method includes providing a spinal implant including first and second bone screws and a body. The body includes a back surface having first and second openings for receiving the first and second screws. The first opening is configured for orientation towards a first vertebral body and the second opening is configured for orientation towards a second vertebral body. The body also includes first and second side surfaces extending from opposing ends of the back surface and first and second end surfaces extending from the respective first and second side surfaces. The ends of the first and second end surfaces meet and define an atraumatic nose. A first angle is formed between the first side surface and the first end surface and a second angle is formed between the second side surface and the first end surface. The first angle is different than the second angle. The method further includes preparing an intervertebral space between the first and second vertebral bodies to receive the spinal implant, inserting the spinal implant into the prepared intervertebral space, and inserting the first and second bone screws through the first and second openings of the spinal implant and into each of the respective first and second vertebral bodies.

In aspects, the method further includes packing a through-bore with biological material. The through-bore is defined by an interior perimeter of the first and second end surfaces, the first and second side surfaces, and the back surface.

In aspects, inserting the first and second bone screws includes inserting at least one plate insert within an insert slot defined in one of a top surface or a bottom surface. The top and bottom surfaces are defined by the back surface, the first and second end surfaces, and the first and second side surfaces, and the insert slot is in communication with an opening of the first and second openings.

In aspects, providing the spinal implant includes the body of the spinal implant having a body portion and a plate, wherein the plate is slidably engageable with the body portion.

In aspects, the method further includes slidably engaging the plate with the body portion to prohibit the plate from moving in a caudal or cephalad direction with respect to the body portion.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 9A is a top view of a bone screw usable with the spinal implant of FIGS. 1 and 6;

FIG. 9B is a side view of the bone screw of FIG. 9A; and

FIG. 9C is a side, cross-sectional view of the bone screw of FIG. 9A taken alone line 9C-9C.

DETAILED DESCRIPTION

Figure 1:
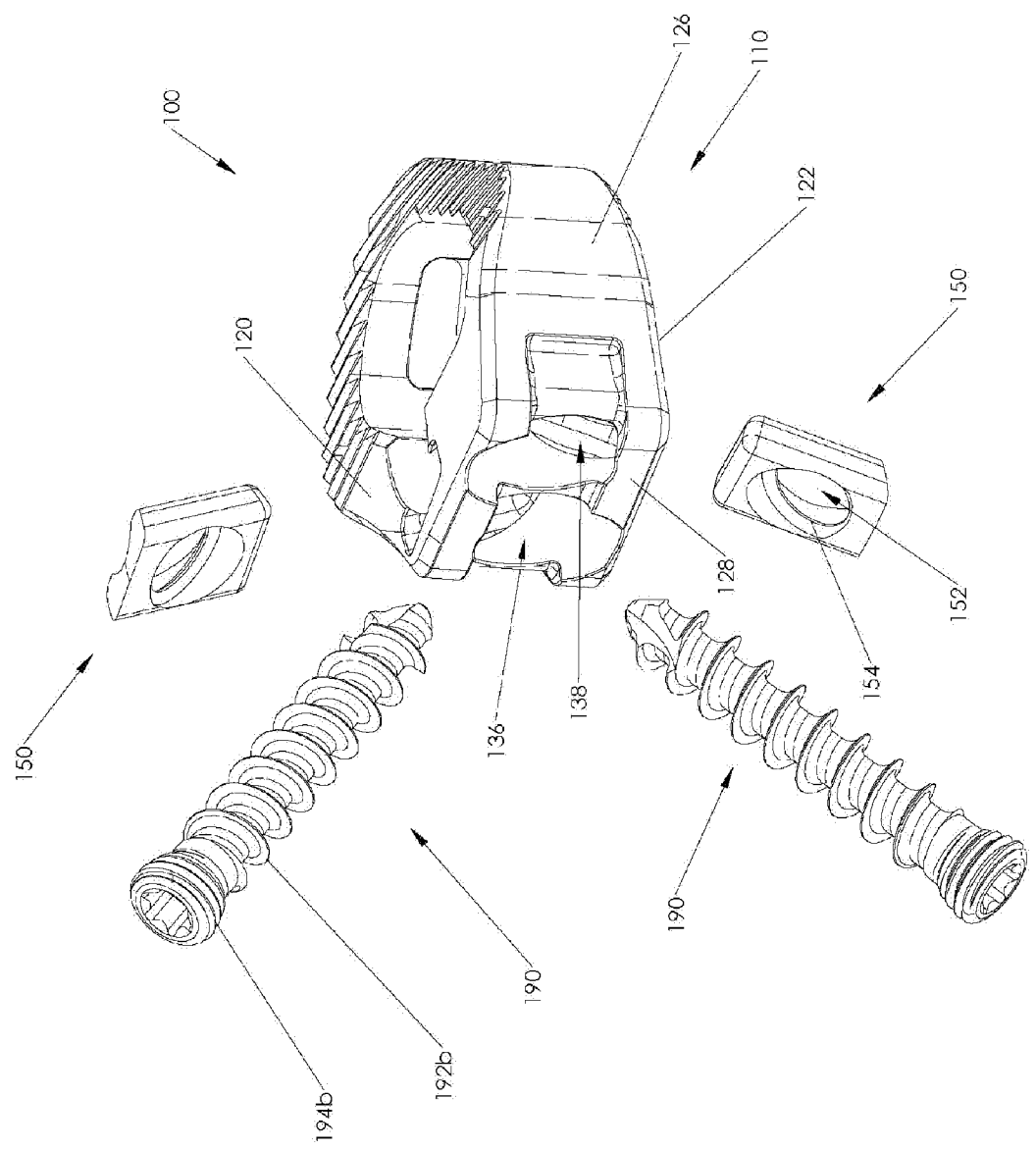
FIG. 1 is a rear, perspective view, of a spinal implant provided in accordance with the present disclosure, with parts separated.

Embodiments of the present disclosure are now described in detail with reference to the drawings in which like reference numerals designate identical or corresponding elements in each of the several views. As commonly known, the term "clinician" refers to a doctor, a nurse, or any other care provider and may include support personnel. Additionally, the term "proximal" refers to the portion of the device or component thereof that is closer to the clinician and the term "distal" refers to the portion of the device or component thereof that is farther from the clinician. In addition, the term "cephalad" is used in this application to indicate a direction toward a patient's head, whereas the term "caudal" indicates a direction toward the patient's feet. Further still, for the purposes of this application, the term "lateral" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Referring now to the drawings, FIGS. 1-5 illustrate one embodiment of a spinal implant provided in accordance with the present disclosure generally identified by reference numeral 100. Spinal implant 100 generally includes a body 110, a plurality of plate inserts 150, and a plurality of bone screws 190. Bone screws 190 are configured for securing spinal implant 100 in a position relative to the adjacent vertebral bodies. Plate inserts 150 cooperate with body 110 to retain bone screws 190 therein, as will be discussed in detail hereinbelow. Each of these components along with the assembly and insertion of spinal implant 100 into the intervertebral space between adjacent vertebral bodies will be described in turn hereinbelow.

The various components of expandable spinal implant 100, or portions thereof, may be formed from various similar or different materials, depending on a particular purpose. In particular, body 110 may be formed from a non-metallic material (e.g., polymeric materials such as polyetheretherketone (PEEK), carbon fiber, etc.), organic materials such as bone, a metallic material (e.g., titanium, titanium alloy, stainless steel, or cobalt chrome (CoCr)), or a ceramic material. Bone screws 190 may be formed from titanium, titanium alloy, CoCr or other suitable metal that is compatible with expandable spinal implant 100. Additionally, plate inserts 150 may be formed from any softer compatible material than that of bone screw 190, such as unalloyed titanium (e.g., commercially pure titanium).

Figure 4:
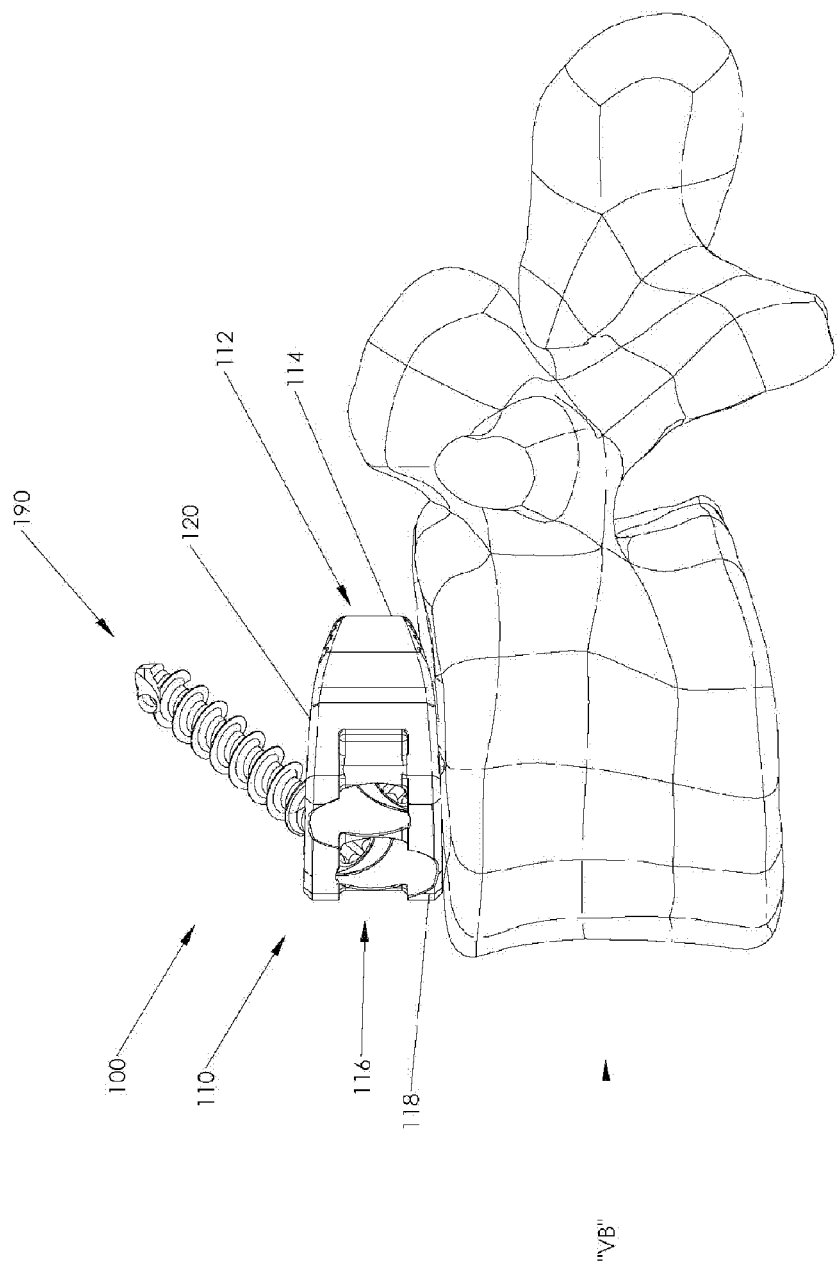
FIG. 4 is a side view of the spinal implant of FIG. 1, coupled to a vertebral body.
Figure 5:
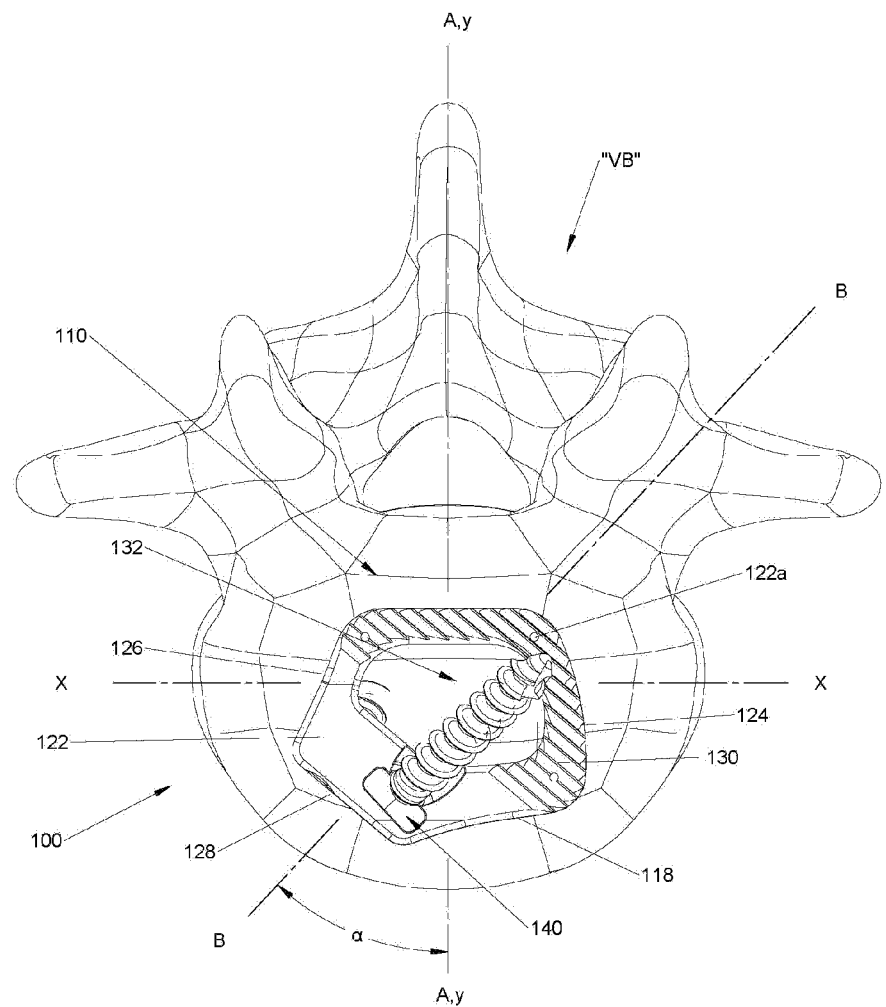
FIG. 5 is a bottom view of the spinal implant and vertebral body of FIG. 4.

Body 110 is illustrated as having a generally pentagonal shape (FIG. 5); however, it is contemplated that body 110 may include other shapes, such as square, rectangular, circular, oval, or the like. As best illustrated in FIG. 4, body 110 includes a substantially planar, first end surface 114, at a distal or leading end 112, and a second end surface 118, opposite thereto at a proximal or trailing end 116, having a substantially planar configuration. As shown in FIG. 2, first end surface 114 defines axis A-A oriented normal thereto and extending through second end surface 118, thereby bisecting first end surface 114. Although shown as generally forming a diverging angle with respect to first end surface 114, it is contemplated that second end surface 118 may define a substantially parallel configuration relative to first end surface 114 (FIG. 5). Body 110 extends between first and second end surfaces 114, 118 to define respective top and bottom surfaces 120 and 122 (FIG. 1), respectively, as well as opposed side surfaces 124 and 126 (FIG. 5). Top and bottom surfaces 120, 122 are illustrated as being substantially parallel to each other; however, it is contemplated that top surface 120 may be planar, convex, or the like, and top surface 120 may approximate bottom surface 122, or vice versa in order to provide a desired amount of lordosis. Opposing side surfaces 124 and 126 may form an oblique angle with respect to first end surface 114, such that body 110 increases in width in a proximal direction along axis A-A. As best illustrated in FIG. 5, although shown as having a curvate profile when viewed from above, it is contemplated that side surface 124 may include any suitable profile, such as planar. Side surface 126 is generally shown has having a substantially planar configuration when viewed from above, and defines an angle with respect to first end surface 114 that is greater than the angle that side surface 124 defines with first end surface 114 (i.e., the angle formed by side surface 124 and first end surface 114 is more acute than the angle formed by side surface 126 and first end surface 114). In this respect, body 110 is asymmetrical about axis A-A with the relative width of body 110 being greater on the side of side surface 126 than that of side surface 124. It is contemplated that the angle defined by side surface 126 and first end surface 114 is between 90 and 110 degrees, whereas the angle defined by side surface 124 and first end surface 114 is between 110 and 160 degrees. Oblique end surface (back surface) 128 is interposed between second end surface 118 and side surface 126, and defines a generally planar configuration including axis B-B extending perpendicular thereto (FIG. 2), thereby bisecting oblique end surface 128. Oblique end surface 128 is oriented relative to first end surface 114 such that axis B-B (FIG. 2) defines an angle α relative to axis A-A between 20 degrees and 60 degrees. In one embodiment, the angle α of axis B-B relative to axis A-A is 40 degrees.

As illustrated in FIG. 5, body 110 is configured such that each of side surfaces 124, 126 and oblique end surface 128 define a substantially atraumatic blunt nose profile with respect to each other and first and second end surfaces 114, 118. The intersection of top and bottom surfaces 120, 122 with each of side surfaces 124, 126 and oblique end surface 128 may be rounded to enhance the atraumatic character of body 110.

Figure 3:
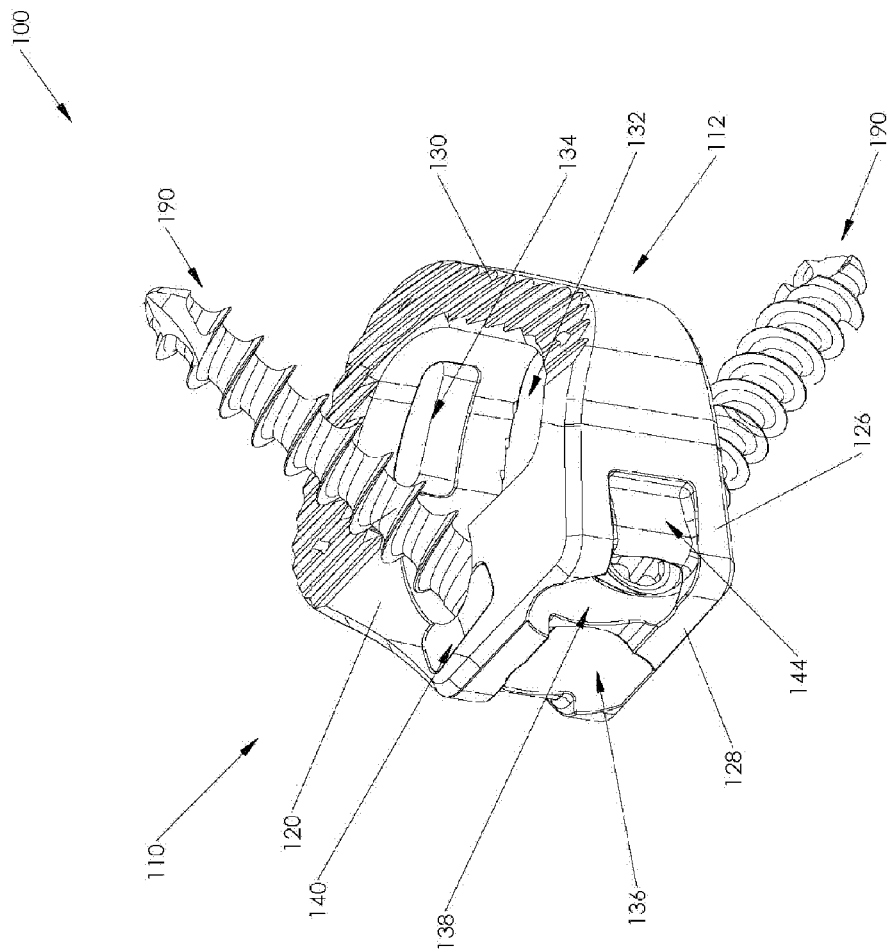
FIG. 3 is a side, perspective view, of the spinal implant of FIG. 2.

Referring now to FIGS. 3 and 5, top surface 120 and bottom surface 122 include a plurality of ridges 130 arranged thereon. Although generally as shown as being disposed on the leading half of top and bottom surfaces 120, 122, it is contemplated that ridges 130 may be disposed on any suitable portion of top and bottom surfaces 120, 122. In this manner, the leading half (e.g. adjacent the leading end 112) of top and bottom surfaces 120, 122 may include ridges, whereas the trailing half, including the insert slot 140 (e.g. adjacent the trailing end 116) may be devoid of ridges. Ridges 130 are configured to frictionally engage an adjacent surface of a vertebral body (i.e., a vertebral endplate) to maintain spinal implant 100 in a position relative to the adjacent vertebral body and to inhibit spinal implant 100 from backing out of the intervertebral space since ridges 130 will bite into the vertebral endplate. As can be appreciated, ridges 130 may take any suitable form capable of engaging a surface of a vertebral body, such as teeth, texturing, surface roughness patterning, projections, and the like. As best illustrated in FIG. 5, ridges 130 are arranged in a parallel configuration relative to oblique end surface 128, thereby forming an oblique angle with first end surface 114. It is contemplated that ridges 130 may be oriented in any suitable configuration relative to first end surface 114.

As best illustrated in FIG. 5, bottom surface 122 includes at least one aperture 122*a* defined therein and at least partially penetrating therethrough configured to receive an optional fiduciary insert (not shown), thus allowing the orientation of spinal implant 100 to be determined using a number of different imaging modalities as are known in the art. This feature is particularly important when spinal implant 100 is made from a substantially radiolucent material (e.g., PEEK). It is contemplated that top and bottom surfaces 120, 122 may include additional apertures 122*a*.

Body 110 includes a through-bore 132 defined through top and bottom surfaces 120, 122. Although generally shown as having a configuration similar to that of the overall outer profile of body 110, it is contemplated that through-bore 132 may have any suitable shape, such as square, rectangular, circular, or the like. As can be appreciated, through-bore 132 is configured to receive biological material, such as bone in-growth material, drugs, or other suitable materials or compounds. Examples of such materials are allograft material, autograft material, calcium phosphate/bone marrow aspirate (BMA), autogenous bone material, or synthetic materials comprised of a biocompatible, osteoconductive, osteoinductive, or osteogeneic material such as VITOSS® Synthetic Cancellous Bone Void Filler material.

As best illustrated in FIG. 3, lumen 134 is defined through side surface 124 and an interior surface of through-bore 132. Although generally shown as having a substantially quadrilateral configuration, lumen 134 may have any suitable configuration such as circular, square, rectangular, or the like.

Referring back to FIG. 1, first and second screw holes 136, 138 extend through oblique end surface 128. Screw hole 136 is obliquely angled relative to oblique end surface 128 and is oriented toward top surface 120 (e.g., first screw hole 136 extends in a non-perpendicular orientation relative to oblique end surface 128) thereby directing bone screw 190 therethrough at a similar oblique angle towards one of the vertebral bodies "VB" (FIG. 4) for engagement of bone screw 190 within the vertebral body "VB". Second screw hole 138 is configured in a similar fashion to that of first screw hole 136, however, second screw hole is obliquely angled relative to oblique end surface 128 towards bottom surface 122. First and second screw holes 136, 138 are arranged in a side-by-side configuration. Although generally shown as having two screw holes, it is contemplated that body 110 may include any suitable number of screw holes for coupling body 110 to a vertebral body. It is contemplated that only one bone screw may be used in a particular application while in other situations three or more screws may be used in varying orientations for coupling body 110 to one or two adjacent vertebral bodies. As such, the bone screws may be oriented towards a single vertebral body or the bone screws may be arranged such that they engage both adjacent vertebral bodies.

With reference to FIGS. 3 and 5, an insert slot 140 is defined in top surface 120 commutating with first screw hole 136. A corresponding insert slot is defined in bottom surface 122 (FIG. 5) and is configured to communicate with second screw hole 138. In the interest of brevity, only insert slot 140 will be described in detail herein, although both are substantially identical. Insert slot 130 is configured to receive a plate insert 150 therein. Insert slot 140 is dimensioned such that plate insert 150 and insert slot 140 engage in an interference fit, thereby retaining plate insert 150 within insert slot 140. However, it is contemplated that insert slot 140 may be dimensioned to slidably receive plate insert 150. It is contemplated that plate insert 150 may be retained within insert slot 140 by any suitable bonding means known in the art (e.g., adhesives, welding, etc.). It is contemplated that each screw hole (i.e., first and second screw holes 136, 138, or any suitable combination thereof) will have a corresponding insert slot 140 for retaining a respective bone screw 190 therein.

Figure 2:
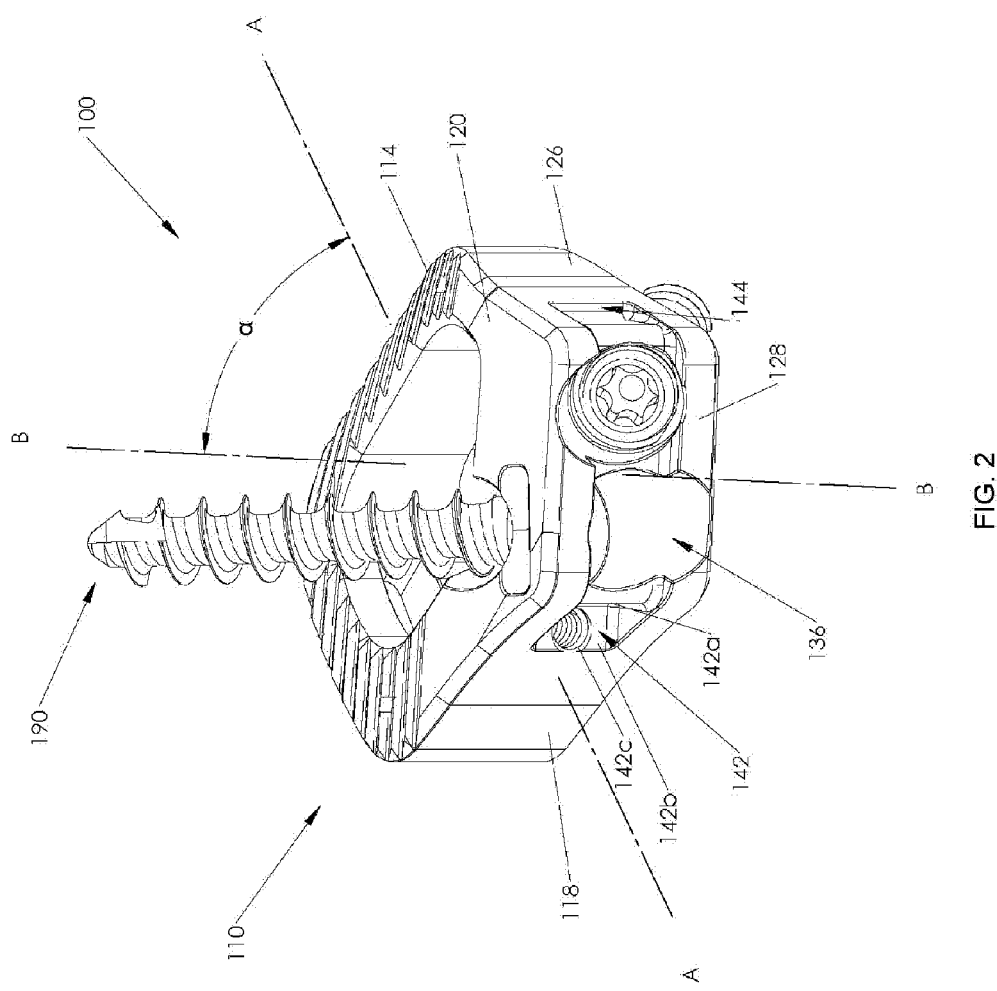
FIG. 2 is a rear, perspective view, of the assembled spinal implant of FIG. 1.

As shown in FIG. 1, plate insert 150 includes a screw opening 152 defined therethrough and an annular sidewall extending downward from a top surface thereof to form a corresponding lip 154 proximate a bottom surface thereof. In operation, when plate insert 150 is inserted in a corresponding insert slot 140, screw opening 152 substantially aligns with a corresponding screw hole 136, 138 or is otherwise coincident therewith to permit bone screw 190 to be advanced therethrough. Although described with reference to screw hole 136, the use of plate insert 150 is equally applicable to screw hole 138, and therefore in the interest of brevity, any description thereof will not be discussed in detail herein. As bone screw 190 is advanced through screw hole 136, thread 194b of bone screw 190 threadingly engages lip 154, thereby retaining bone screw 190 within screw hole 136 and preventing bone screw 190 from backing out of screw hole 136. In particular, bone screw 190 may be formed from titanium alloy (e.g., Ti-6Al-4V) and the lip 154 may be formed of a softer compatible material, such as unalloyed titanium. As the lip 154 is formed from a softer material than the bone screw 190, advancement of bone screw 190 through screw hole 136 results in the thread 194b deforming the lip 154 such that the bone screw 190 resists backing out of the screw hole 136. It is further contemplated that any suitable locking means may be employed to retain bone screws 190 within first and second screw holes 136, 138, such as expanding head screws, spring locking clips, cover plates, and the like.

With reference to FIG. 2, body 110 includes a first recess 142 defined in second end surface 118 and adjacent to first screw hole 136. First recess 142 includes a tapered surface 142a that extends towards throughbore 132 and penetrates oblique end surface 128. Tapered surface 142a tapers in a distal direction and increases in depth such that the distal end of first recess 142 is more defined than the proximal end (i.e., the proximal end is almost flush with second end surface 118, whereas the distal end provides a deep recess). First recess terminates in a planar surface 142b on a distal end and includes a threaded bore 142c is defined therein. Threaded bore 142c is configured to threadably engage a suitable insertion instrument (not shown), as will be discussed in further detail hereinbelow.

As best illustrated in FIG. 3, a second recess 144 is defined in side surface 126 and penetrates oblique end surface 128. Second recess 144 is identical to that of first recess 142, except second recess 144 is in a mirrored configuration to that of first recess 142 about axis B-B. Although generally shown as not including a threaded bore, it is contemplated that second recess 144 may include a threaded bore configured to engage a suitable insertion instrument similarly to that of first recess 142. First and second recesses 142, 144 cooperate to releasably engage opposing prongs of a suitable insertion instrument (not shown), thereby permitting a suitable insertion instrument (not shown) to grasp spinal implant 100 and maneuver spinal implant 100 to a suitable location within the intervertebral space, as will be discussed in further detail hereinbelow.

Referring now to FIGS. 9A-9C, an illustration of bone screw 190 configured for use with spinal implant 100 is shown. As can be appreciated, a plurality of bone screws 190 is configured to secure body 110 of spinal implant 100 to adjacent vertebral bodies. However, as bone screws 190 are similar to one another, only one is described in detail herein. It is also contemplated that other suitable bone screws 190 be provided for use with spinal implant 100.

Bone screw 190 generally includes a shank 192 and a head 194. Shank 192 defines a distal tip 192a and pitched threading 192b disposed about shank 192. Distal tip 192a and pitched threading 192b facilitate driving bone screw 190 into bone and securement of bone screw 190 therein. Head 194 of bone screw 190 defines a tool-engaging recess 194a. Head 194 further includes a thread 194b for threadably engaging lip 154 of plate insert 150. Pitched threading 192a has a pitch greater than that of thread 194b. Tool-engaging recess 194a may have any shape and/or dimension suitable for transmitting rotational motion from a tool to bone screw 190 (e.g., square, hex, pozidrive, or the like).

For a detailed discussion of the construction of exemplary bone screws, reference may be made to U.S. Patent Application Publication No. 2014/0214166, the entire contents of which are incorporated herein by reference.

With reference to FIGS. 1-6, the insertion of a spinal implant 100 into the intervertebral space between adjacent vertebral bodies "VB" during the course of a spinal surgical procedure is described. Initially, the intervertebral space is prepared, e.g., damaged or diseased tissue is partially or totally removed. Thereafter, the interior space of throughbore 132 of body 110 may be packed with biological material such as bone in-growth material, drugs, or other suitable materials or compounds. Examples of such materials are allograft material, autograft material, calcium phosphate/bone marrow aspirate (BMA), autogenous bone material, or synthetic materials comprised of a biocompatible, osteoconductive, osteoinductive, or osteogeneic material such as VITOSS® Synthetic Cancellous Bone Void Filler material. Next, spinal implant 100 is affixed to a suitable insertion instrument by releasably engaging first and second recesses 142, 144, and thereafter, threadably engaging threaded bore 142c to releasably retain body 110 thereto. At this point, each of plate inserts 150 may be advanced within a respective slot 140 of body 110 and thereafter, retained to body 110 by any suitable means discussed hereinabove. Spinal implant 100 may then be advanced into a previously prepared intervertebral space of the patient's spine. Typically, an incision is created through the patient's skin and tissue is atraumatically moved to create a working space for an anterior approach. It is contemplated that a lateral approach or an anterior-lateral approach may be employed. As best illustrated in FIG. 5, spinal implant 100 is oriented such that axis A-A lies substantially parallel with an axis Y-Y defined along the midsagittal plane of the spine, and substantially normal to an axis X-X defined along the transverse plane of the spine. In this orientation, the angle of oblique end surface 128 with respect to axis A-A, Y-Y permits easier access to bone screw holes 136, 138, and thereafter, bone screws 190 when driving bone screws 190 into a respective adjacent vertebral body "VB". Bone screws 190 (FIGS. 9A-9C) are then inserted through respective screw holes 136, 138 of body 110 and are driven into one of the adjacent vertebral bodies. Due to the obliquely angled configuration of screw holes 136, 138 relative to oblique end surface 128 mentioned above, bone screws 190 are guided through screw holes 136, 138 and into the vertebral body "VB".

Figure 6:
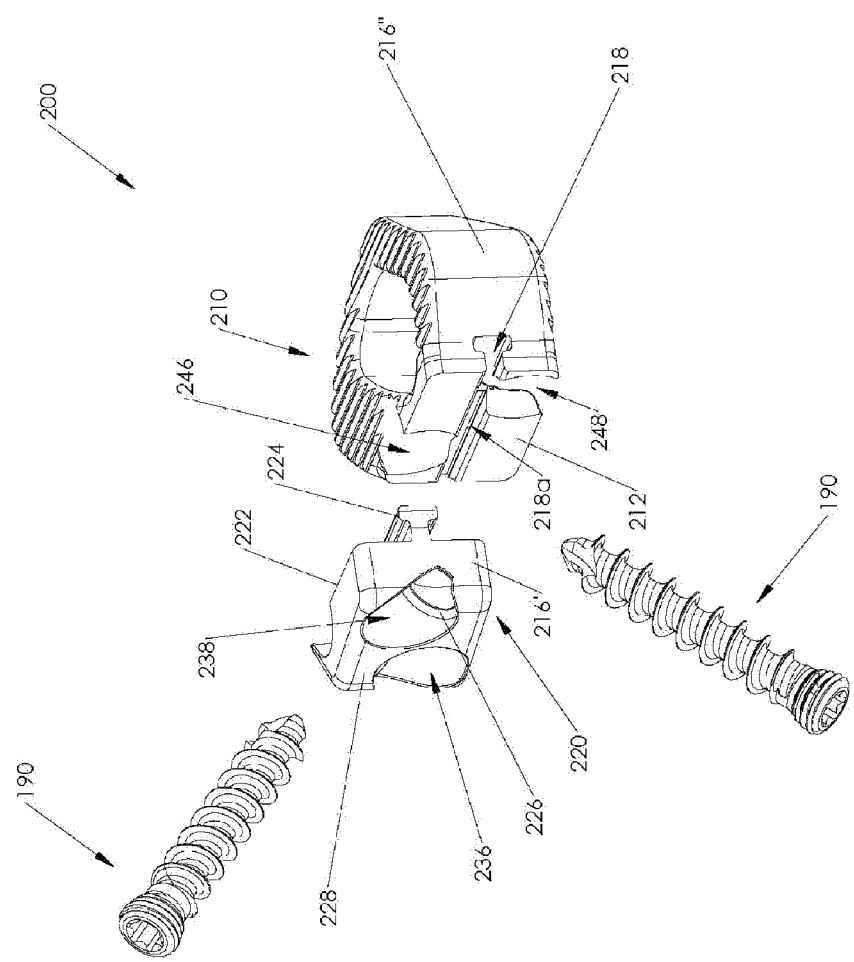
FIG. 6 is a rear, perspective view, of another spinal implant provided in accordance with the present disclosure, with parts separated.
Figure 7:
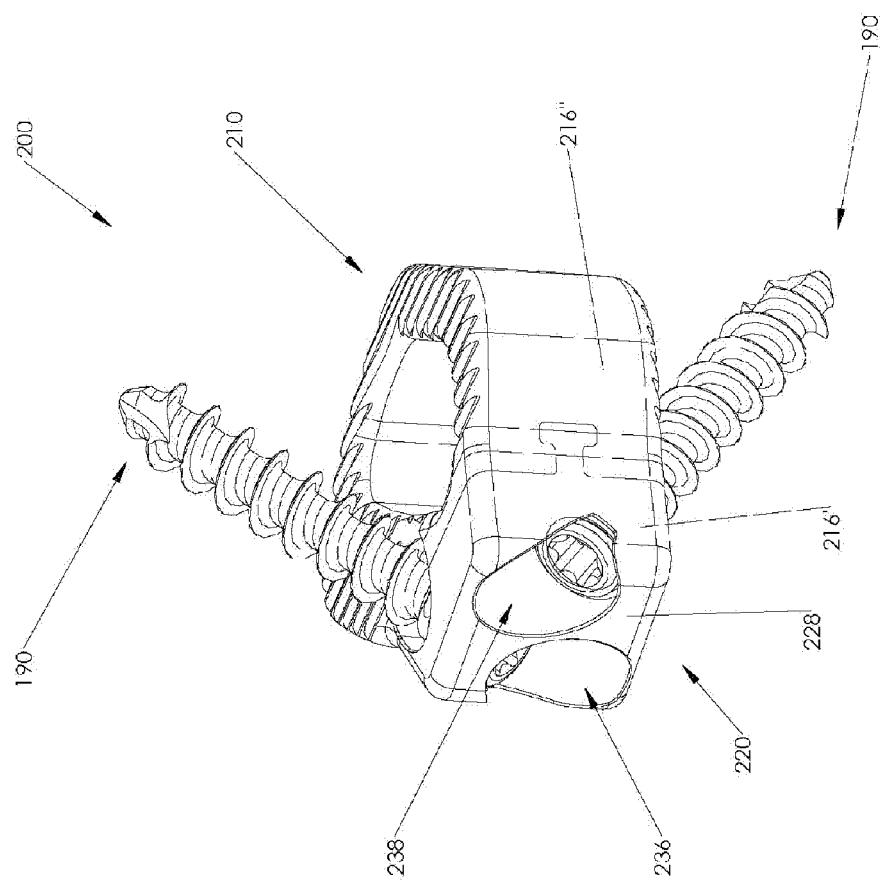
FIG. 7 is a rear, perspective view, of the assembled spinal implant of FIG. 6.
Figure 8:
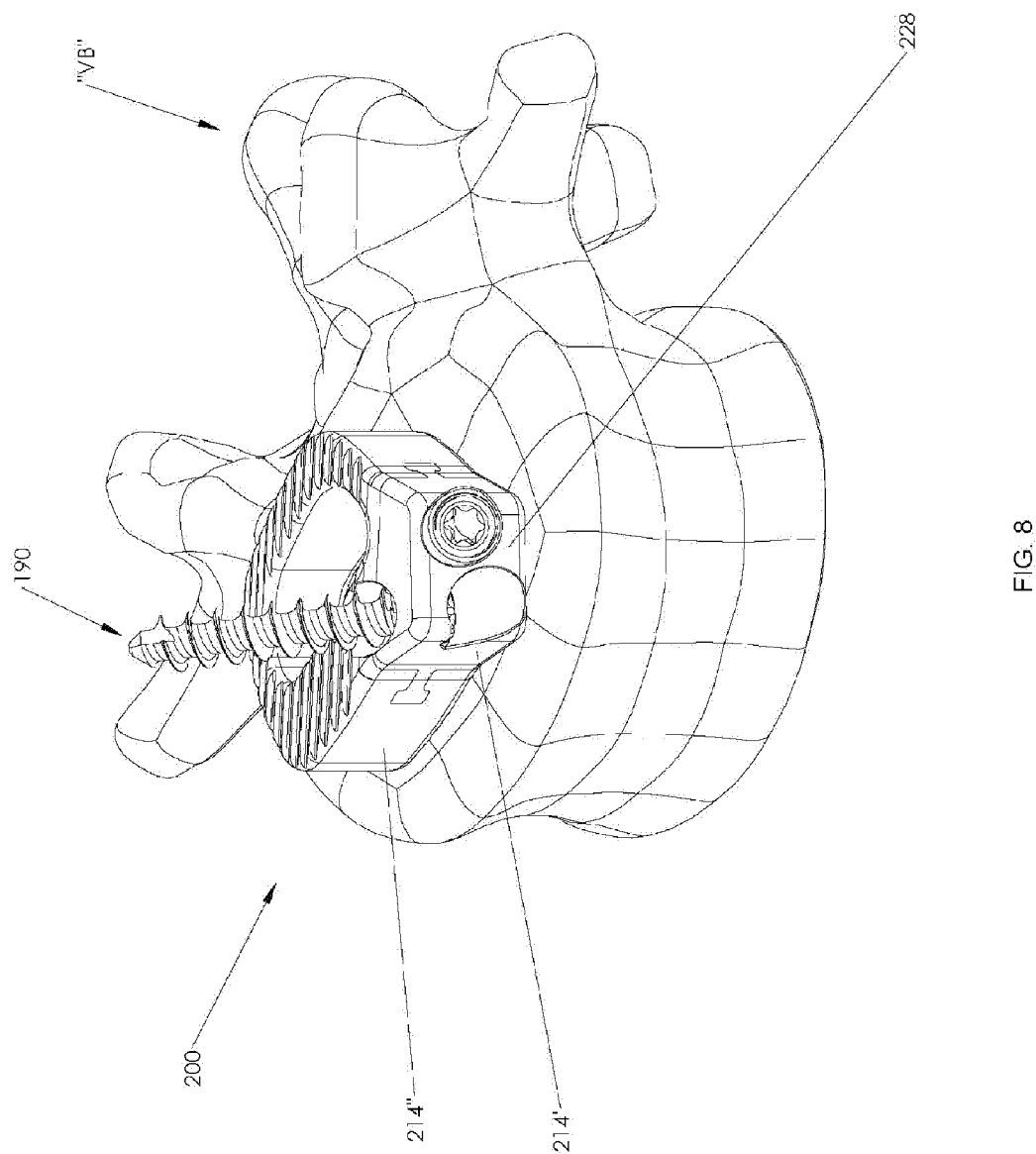
FIG. 8 is a rear, perspective, view of the spinal implant of FIG. 6 coupled to a vertebral body.

Referring now to FIGS. 6-8, another embodiment of a spinal implant in accordance with the present disclosure is shown, generally referred to as spinal implant 200. Spinal implant 200 is substantially similar to spinal implant 100, and therefore, in the interest of brevity, only the differences between spinal implant 200 and spinal implant 100 will be described in detail hereinbelow.

In this embodiment, as illustrated in FIG. 6, spinal implant 200 includes a body portion 210 and a plate 220 which cooperate to define two-part spinal implant 200 configured for positioning between adjacent vertebral bodies. It is contemplated that body portion 210 may be formed from a non-metallic material (e.g., polymeric materials such as polyetheretherketone (PEEK), carbon fiber, etc.), organic materials such as bone, whereas plate 220 may before formed from a different material such as a metallic material (e.g., titanium, titanium alloy, stainless steel, or cobalt chrome (CoCr)) or a ceramic material and vice versa.

Continuing with FIG. 6, plate 220 defines a leading surface 222 disposed opposite oblique end surface 228 (comparable to oblique end surface 128 of body 110 of spinal implant 100) and oriented substantially parallel thereto. T-shaped projection 224 is disposed on leading surface 222 and extends between side surfaces 214' (FIG. 8) and 216' (comparable to the trailing ends of side surfaces 124, 126 of body 110 of spinal implant 100) and facilitates selective attachment to body portion 210, as illustrated in FIG. 7.

Body portion 210 defines trailing surface 212 disposed adjacent to and mirroring leading surface 222 of plate 220. A T-shaped slot 218 is defined through side surfaces 214" (FIG. 8) and 216" (corresponding to the leading ends of side surfaces 124, 126 of body 110 of spinal implant 100) and includes a profile corresponding to the profile of T-shaped projection 224. T-shaped slot 218 includes an opening 218a defined through trailing surface 212 thereby permitting T-shaped projection 224 to engage T-shaped slot 218 in order to facilitate selective attachment of body portion 210 and plate 220 in a dovetail configuration by sliding plate 220 in a direction from either side surface 214" or 216". This configuration limits relative vertical movement (i.e., cephalad or caudal) between plate 220 and body portion 210.

As best illustrated in FIG. 6, screw holes 236, 238 are defined in oblique surface 228 (comparable to screw holes 136, 138, respectively, of body 110 of spinal implant 100) and include a lip 226 defined on the inner surface thereof. Screw holes 236, 238 are substantially similar to that of screw holes 136, 138, respectively, and therefore only the differences therebetween will be discussed herein. Lip 226 is substantially similar in structure to lip 154 of plate 150 and operates in a substantially similar fashion, and therefore, in the interest of brevity, further details will not be discussed hereinbelow. It is further contemplated that any suitable locking means may be employed to retain bone screws 190 within first and second screw holes 236, 238, such as expanding head screws, spring locking clips, cover plates, and the like. Similarly to spinal implant 100, spinal implant 200 may include any suitable number of screw holes for coupling body 110 to a vertebral body. It is contemplated that only one bone screw may be used in a particular application while in other situations three or more screws may be used in varying orientations for coupling spinal implant 200 to one or two adjacent vertebral bodies. As such, the bone screws may be oriented towards a single vertebral body or the bone screws may be arranged such that they engage both adjacent vertebral bodies.

Continuing with FIG. 6, body portion 210 further includes a pair of annular grooves 246, 248, which are defined through trailing surface 212 and are aligned axially with screw holes 236, 238, respectively, to permit passage of bone screws 190 therethrough (FIG. 7).

With reference to FIG. 8, spinal implant 200 may be utilized in a similar respect to spinal implant 100 as detailed above, with the exception that body portion 210 and plate 220 are initially engaged with each other by sliding T-shaped projection 224 of plate 220 into T-shape slot 218 of body portion 210 before insertion into a previously prepared intervertebral space of the patient's spine. Typically, an incision is created through the patient's skin and tissue is atraumatically moved to create a working space for an anterior approach. It is contemplated that a lateral approach or an anterior-lateral approach may be employed. As each of screw holes 236, 238 include a corresponding lip 226, plate inserts 150 are unnecessary.

It will be understood that various modifications may be made to the embodiments of the presently disclosed expandable spinal implant. Therefore, the above description should not be construed as limiting, but merely as exemplifications of embodiments. Those skilled in the art will envision other modifications within the scope and spirit of the present disclosure.

What is claimed is:
1. A spinal implant, comprising:
first and second bone screws; and
a body including:
a planar back surface having first and second openings for receiving the first and second bone screws, the first opening configured for orientation towards a first vertebral body and the second opening configured for orientation towards a second vertebral body;
first and second end surfaces extending from opposing ends of the back surface, the first and second end surfaces defining a divergent angle with respect to one another;
first and second side surfaces extending from the respective first and second end surfaces, wherein ends of the first and second side surfaces meet and define an atraumatic nose, wherein the first side surface defines a first longitudinal axis extending perpendicular thereto, the first longitudinal axis bisecting the first side surface, wherein the body is asymmetrical about the first longitudinal axis;
a first angle formed between the first side surface and the first end surface;

a second angle formed between the second side surface and the first side surface, the second angle being less than the first angle;

wherein the back surface defines a second longitudinal axis extending perpendicular thereto, the back surface oriented relative to the first side surface such that the second longitudinal axis defines an oblique angle with respect to the first longitudinal axis, first and second insert slots each defined in one of the top and bottom surfaces such that the first insert is disposed on one side of the second longitudinal axis and the second insert slot is disposed on an opposite side of the second longitudinal axis, the first and second insert slots being in communication with corresponding openings of the first and second openings and configured to receive plate inserts, each plate insert including a screw opening defined therethrough and configured to be received within one of the first and second insert slots with the screw opening substantially aligned with a corresponding opening of the first and second openings of the body, wherein the first and second openings are disposed parallel to a plane containing the second longitudinal axis, the back surface, the first and second end surfaces, and the first and second side surfaces define top and bottom surfaces, each of the top and bottom surfaces has a first portion and a second portion, wherein the second portions are proximate to the back surface, the first portions of the top and bottom surfaces include ridges adapted to engage first and second vertebral bodies and the second portions of the top and bottom surfaces lack ridges.

2. The spinal implant of claim 1, wherein a through-bore is defined through the top and bottom surfaces of the body.

3. A method of performing surgery, comprising:
preparing an intervertebral space between first and second vertebral bodies to receive a spinal implant;
inserting the spinal implant of claim 1 into the prepared intervertebral space; and
inserting the first and second bone screws through the first and second openings of the spinal implant and into each of the respective first and second vertebral bodies.

4. The method of claim 3, further including packing a through-bore with biological material, the through-bore defined by an interior perimeter of the first and second end surfaces, the first and second side surfaces, and the back surface.

5. The method of claim 3, wherein the step of inserting the first and second bone screws further includes inserting at least one plate insert within an insert slot defined in one of a top surface or a bottom surface, the top and bottom surfaces defined by the back surface, the first and second end surfaces, and the first and second side surfaces, the insert slot being in communication with an opening of the first and second openings.

* * * * *